United States Patent [19]

Breitenstein et al.

[11] Patent Number: 4,483,707

[45] Date of Patent: Nov. 20, 1984

[54] PHENYLAMINO-OXO-ACETIC ACIDS AND ESTERS THEREOF AS ANTIDOTES FOR PROTECTING CULTIVATED PLANTS FROM THE PHYTOTOXIC ACTION OF AGGRESSIVE HERBICIDES

[75] Inventors: Werner Breitenstein; Werner Föry; Robert Nyfeler, all of Basel, Switzerland; Manfred Böger, Weil am Rhein, Fed. Rep. of Germany

[73] Assignee: Ciba-Geigy Corporation, Ardsley, N.Y.

[21] Appl. No.: 462,257

[22] Filed: Jan. 31, 1983

[30] Foreign Application Priority Data

Feb. 11, 1982 [CH] Switzerland ............... 854/82

[51] Int. Cl.³ .................. A01N 43/40; A01N 37/44
[52] U.S. Cl. ........................... 71/94; 71/92; 71/93; 71/105; 71/111; 560/43
[58] Field of Search ............ 560/43; 71/111, 92, 71/93, 94, 95

[56] References Cited

U.S. PATENT DOCUMENTS 3,317,584  5/1967  Stoffel ............... 560/43 X
3,511,804  5/1970  Duennenberger et al. ...... 560/43 X
4,230,484 10/1980  Batch et al. ............... 71/111

OTHER PUBLICATIONS

Baruffini et al., Il Farmaco, vol. 22, No. 9, (1967), 717-734.

Primary Examiner—Bernard Helfin
Attorney, Agent, or Firm—Frederick H. Rabin; Bruce M. Collins

[57] ABSTRACT

Phenylamino-oxo-acetic acids and the esters thereof, of the formula I

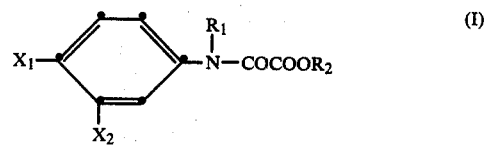

wherein
$X_1$ and $X_2$, each independently of the other, are halogen or halomethoxy, or one of $X_1$ and $X_2$ is also hydrogen,
$R_1$ is hydrogen or $C_1-C_4$alkyl, and
$R_2$ is hydrogen or an unsubstituted or substituted $C_1-C_{18}$alkyl, $C_3-C_{18}$alkenyl, $C_3-C_6$alkynyl or $C_3-C_8$cycloalkyl radical, are able to protect cultivated plants from the phytotoxic action of aggressive herbicides. Preferred herbicides are those of the classes of α-(phenoxyphenoxy)propionic acid and α-(pyridyloxyphenoxy)propionic acid derivatives. The cultivated plants to be protected are primarily monocots, i.e. cereals.

6 Claims, No Drawings

PHENYLAMINO-OXO-ACETIC ACIDS AND ESTERS THEREOF AS ANTIDOTES FOR PROTECTING CULTIVATED PLANTS FROM THE PHYTOTOXIC ACTION OF AGGRESSIVE HERBICIDES

The present invention relates to a composition for and a method of protecting cultivated plants from the phytotoxic action of aggressive herbicides. The method of this invention comprises applying phenylamino-oxo-acetic acids of the formula I below or esters thereof, simultaneously or in quick succession, with the herbicide to the cultivated plants, or applying a composition which contains, in addition to the herbicide, a phenylamino-oxo-acetic acid of the formula I or an ester thereof. The invention also relates to the compositions which contain phenylamino-oxo-acetic acids of the formula I and esters thereof.

The phenylamino-oxo-acetic acids and esters thereof have the formula I

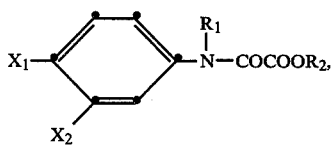

wherein
$X_1$ and $X_2$, each independently of the other, are halogen or halomethoxy, or one of $X_1$ and $X_2$ is also hydrogen,
$R_1$ is hydrogen or $C_1$–$C_4$ alkyl, and
$R_2$ is hydrogen or an unsubstituted or substituted $C_1$–$C_{18}$alkyl, $C_3$–$C_{18}$alkenyl, $C_3$–$C_6$alkynyl or $C_3$–$C_8$cycloalkyl radical.

In the above definition, $R_2$ may have the following meanings: hydrogen, unsubstituted $C_1$–$C_{18}$alkyl, $C_3$–$C_{18}$alkenyl, or $C_3$–$C_8$cycloalkyl; or $C_1$–$C_6$alkyl, $C_3$–$C_6$alkenyl or $C_3$–$C_6$cycloalkyl radicals which are substituted by $[C_2$–$C_3$alkylene-O$]_nR'$, wherein n is 1 or 2 and $R'$ is hydrogen or $C_1$–$C_6$ alkyl; or by $C_1$–$C_6$alkylthio, $C_1$–$C_6$hydroxyalkylthio, $C_1$–$C_6$alkoxycarbonyl, $C_1$–$C_6$alkylthiocarbonyl, $C_1$–$C_6$alkylcarbonyl, amino, $C_1$–$C_6$alkylamino, $C_1$–$C_6$dialkylamino, a saturated 5- or 6-membered heterocyclic ring which is bound through the nitrogen atom and which may contain an additional nitrogen, oxygen or sulfur atom in the ring, a $C_1$–$C_{18}$alkylcarbonyloxy or $C_3$–$C_{18}$alkenylcarbonyloxy group, carbamoyl, $C_1$–$C_4$alkylcarbamoyl, $C_1$–$C_4$dialkylcarbamoyl or a saturated 5- or 6-membered heterocyclic ring which is linked to a carbamoyl group and which may contain an additional nitrogen, oxygen or sulfur atom, or phenyl which is unsubstituted or substituted by halogen, cyano, $C_1$–$C_6$alkyl, $C_1$–$C_6$haloalkyl, $C_1$–$C_6$alkoxy, $C_1$–$C_6$alkylthio, $C_1$–$C_6$alkylcarbonyl, $C_1$–$C_6$alkoxycarbonyl, amino, $C_1$–$C_6$alkylamino, $C_1$–$C_6$dialkylamino, carbamoyl, or mono- or di($C_1$–$C_4$)alkylamino or nitro; or $R_2$ is $C_3$–$C_6$alkynyl, unsubstituted or substituted by phenyl which is unsubstituted or substituted by halogen, cyano, $C_1$–$C_6$alkyl, $C_1$–$C_4$haloalkyl, $C_1$–$C_6$alkoxy, $C_1$–$C_6$alkylthio, $C_1$–$C_6$alkylcarbonyl, $C_1$–$C_4$alkoxycarbonyl, amino, $C_1$–$C_6$alkylamino, $C_4$–$C_6$dialkylamino, carbamoyl, $C_1$–$C_6$alkylcarbamoyl, $C_1$–$C_6$dialkylcarbamoyl or nitro.

The term "alkyl" by itself or as moiety of another substituent comprises branched or unbranched alkyl groups which contain the indicated number of carbon atoms. Examples of such alkyl groups are: methyl, ethyl, propyl, isopropyl, butyl, isobutyl, sec-butyl, tert-butyl, and the higher homologues amyl, isoamyl, hexyl, heptyl, octyl etc., together with their isomers. The alkenyl or alkynyl groups may accordingly be straight chain or branched.

Cycloalkyl groups are cyclopropyl, cyclobutyl, cyclopentyl, cyclohexyl and further groups up to decaline.

The alkenyl and alkynyl groups may also be straight chain or branched and contain one or more unsaturated positions in the radical. Examples of such groups are: allyl, methallyl, propargyl, butenyl, butadienyl, butynyl, butadienyl radicals and the higher homologues thereof.

The phenylamino-oxo-acetic acids of the formula I and the esters thereof are very suitable for protecting cultivated plants from attack by aggressive agrochemicals, especially by herbicides of the most widely varying classes, where such compounds are not tolerated or are insufficiently tolerated by cultivated plants. The cultivated plants to be protected are in particular those which are of importance in the food or textile sector, e.g. sorghum, rice, maize, cereals (wheat, rye, barley, oats), cotton, sugar beet and soybeans.

The herbicides may belong e.g. to one of the following classes of compounds: triazines and triazinones; phenylureas, in particular 3-(4-isopropylphenyl)-1,1-dimethylurea (isoproturon); carbamates and thiocarbamates; haloacetanilides, in particular chloroacetanilides; chloroacetamides; halophenoxyacetates; diphenyl ethers, e.g. substituted phenoxyphenoxyacetates and -amides; substituted pyridyloxyphenoxyacetates and -amides, in particular 2-propynyl 2-[4-(3,5-dichloropyridyl-2-oxy)phenoxy]propionate; benzoic acid derivatives; nitroanilines; oxadiazolones; phosphates; pyrazoles; and sulfonylureas.

Suitable herbicides are e.g. the following individual compounds:

Triazines and triazinones: 2,4-bis(isopropylamino)-6-methylthio-1,3,5-triazine ("prometryn"), 2,4-bis(ethylamino)-6-methylthio-1,3,5-triazine ("symetryn"), 2-(1′,2′-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin"), 2-tert-butylamino-4-ethylamino-6-methylthio-1,3,5-triazine ("terbutryn"), 2-chloro-4-tert-butylamino-6-ethylamino-1,3,5-triazine ("terbuthylazin"), 2-chloro-4-isopropylamino-6-ethylamino-1,3,5-triazine ("atrazin"), 2-tert-butylamino-4-alkylamino-6-methoxy-1,3,5-triazine ("terbumeton").

Phenylureas: N-(3-chloro-4-methylphenyl)-N′,N′-dimethylurea ("chlortoluron"), N-(4-bromophenyl)-N′-methoxy-N′-methylurea ("metobromuron"), N-(4-bromo-3-chlorophenyl)-N′-methoxy-N′-methylurea ("chlorbromuron"), N-(3,4-dichlorophenyl)-N′-methoxy-N′-methylurea ("linuron"), N-(4-chlorophenyl)-N′-methoxy-N′-methylurea ("monolinuron"), N-(3-trifluoromethylphenyl)-M′,N′-dimethylurea ("fluometuron"), N-(3-chloro-4-methoxyphenyl)-N′,N′-dimethylurea ("metoxuron"), N-(4-chlorophenyl)-N′,N′-dimethylurea ("monuron"), N-(3,4-dichlorophenyl)-N′,N′-dimethylurea ("diuron"), N-(benzthiazol-2-yl)-N,N′-dimethylurea ("methabenzthiazuron").

Chloroacetanilides: 2-chloro-2′,6′-diethyl-N-(2″-propoxyethyl)acetanilide ("propalochlor"), 2-chloro-6′- ethyl-N-(2''-methoxy-1''-methylethyl)acet-o-toluidide ("metolachlor"), 2-chloro-2',6'-diethyl-N-(butoxymethyl)acetanilide ("butachlor"), 2-chloro-6'-ethyl-N-(ethoxymethyl)acet-o-toluidide ("acetochlor"), 2-chloro-6'-ethyl-N-(2''-propoxy-1''-methylethyl)acet-o-toluidide, 2-chloro-2',6'-dimethyl-N-(2-methoxy-1''-methylethyl)acetanilide, 2-chloro-2',6'-dimethyl-N-(2''-methoxyethyl)acetanilide ("dimethachlor"), 2-chloro-2',6'-diethyl-N-(pyrazol-1-ylmethyl)acetanilide, 2-chloro-6'-ethyl-N-(pyrazol-1-ylmethyl)-aceto-toluidide, 2-chloro-6'-ethyl-N-(2''-butoxy-1''-methylethyl)acet-o-toluidide ("metazochlor"), 2-chloro-6'-ethyl-N-(2''-butoxyl-1''-(methylethyl)acet-o-toluidide and 2-chloro-2'-trimethylsilyl-N-(butoxymethyl)acetanilide.

Chloroacetamides: N-[1-isopropyl-2-methylpropan-1-yl(1)]-N-(2'-methoxyethyl)-chloroacetamide.

Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifluoromethylbenzene ("oxyfluorfen"), 2',4'-dichlorophenyl-3-methoxy-4-nitrophenyl ether ("chlormethoxynil"), methyl 2-[4'-(2'',4''-dichlorophenoxy)phenoxy]propionate, N-(2'-phenoxyethyl)-2-[5'(2''-chloro-4'''-trifluoromethylphenoxy)-phenoxy]propionamide.

Benzoic acid derivatives: methyl-5-(2',4'-dichlorophenoxy)-2-nitrobenzoate ("bifenox"), 5-(2-chloro-4'-trifluoromethylphenoxy)-2-nitrobenzoic acid ("acifluorfen"), 2,6-dichlorobenzonitrile ("dichlobenil").

Nitroanilines: 2,6-dinitro-N,N-dipropyl-4-trifluoromethylaniline ("trifluralin"), N(1'ethylpropyl)-2,6-dinitro-3,4-xylidine ("pendimethalin").

Oxadiazolones: 5-tert-butyl-3(2',4'-dichloro-5'-isopropoxyphenyl)-1,3,4-oxadiazol-2-one ("oxadiazon").

Carbamates and thiocarbamates: N-(3',4'-dichlorophenyl)-propionanilide ("propanil"), S-4-chlorobenzyldiethylthiocarbamate (benthiocarb"), S-ethyl-N,N-hexamethylenethiocarbamate ("molinate"), S-ethyl-dipropylthiocarbamate ("EPTC"), N,N-di-sec-butyl-S-benzyl-thiocarbamate ®Drepamon), S-(2,3-dichloroallyl)-diisopropylthiocarbamate ("diallate"), 1-(propylthiocarbonyl)-decahydroquinaldine, 5-ethyl-diisobutylthiocarbamate ("butylate").

Sulfonylureas: N-(2-chlorophenylsulfonyl)-N'-(4-methoxy-6-methyl-1,3,5-triazin-2-yl)urea, N-(2-methoxycarbonylphenylsulfonyl)-N'-(4,6-dimethylpyrimidine-2-yl)urea, N-(2,5-dichlorophenylsulfonyl)-N'-(4,6-dimethoxypyrimidin-2-yl)urea or e.g. also the sulfonylureas known from EP-A-44 808 and 44 809.

Phosphates: S-2-methylpiperidinocarbonylmethyl-O,O-dipropylphosphorodithioate ("piperophos").

Pyrazoles: 1,3-dimethyl-4-(2',4'-dichlorobenzoyl)-5-(4'-tolylsulfonyloxy)pyrazole.

The compounds of formula I are especially suitable for protecting cultivated plants from the harmful action of herbicides of the general formula II

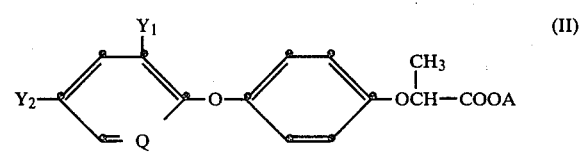

(II)

wherein
Y₁ is hydrogen or halogen,
Y₂ is hydrogen, halogen or trifluoromethyl,
Q is nitrogen or the —CH= group, A is $C_1$–$C_4$alkyl, $C_3$–$C_4$alkenyl, $C_3$–$C_4$alkynyl, $C_2$–$C_8$alkoxyalkyl or an imino radical

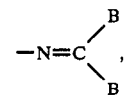

wherein each
B independently of the other is $C_1$–$C_4$alkyl or taken together they are $C_4$–$C_5$alkylene.

Examples of such compounds are: sec-butyl α-[4-(4-chlorophenoxy)phenoxy]propionate, methyl α-[4-(4-trifluoromethylphenoxy)phenoxy]propionare, methyl α-[4-(3,4-dichlorophenoxxy)propionate, acetoxime α-[4-(4-trifluoromethylphenoxy)phenoxypropionate, α-[4-(5-trifluoromethylpyridyl-2-oxy)-phenoxypropionate, α-[4-(3,5-dichloropyridyl-2-oxy)phenoxy]propionic acid, sodium salt, n-butyl α-[4-(5-trifluoromethylpyridyl-2-oxy)phenoxy]propionate and propargyl α-[4-(3,5-dichloropyridyl-2-oxy)phenoxy]propionate, which are known herbicides, where these compounds are not tolerated or are insufficiently tolerated by cultivated plants.

Different compounds which are able to antagonise specifically the harmful action of a herbicide on cultivated plants have already been proposed as antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows or as tank mixture, by themselves or together with the herbicide pre- or postemergence.

Thus, British patent specification No. 1,277,557 discloses the treatment of seed and seedlings of wheat and sorghum with certain esters and amides of oxamic acid before attack by n-methoxymethyl-2',6'-diethyl-chloroacetanilide (alachlor). Other publications (German Offenlegungsschrift specifications Nos. 1 952 910 and 2 245 471, and French patent specification No. 2 021 611), propose antidotes for the treatment of cereals, maize seeds and rice seeds to protect them against attack by herbicidal thiocarbamates. In German patent specification No. 1 576 676 and U.S. Pat. No. 3,131,509, hydroxyaminoacetanilides and hydantoins are suggested for protecting cereal seeds against carbamates such as IPC, CIPC, etc. Further development, however, has shown all these compounds to be unsatisfactory.

The present invention also relates to compositions which contain the phenylamino-oxo-acetic acids of the formula I and esters thereof, together with herbicides.

Depending on the end use, the safener or antidote of the formula I can be used for pretreating seeds of the cultivated plant (dressing of the seeds or seedlings) or it can be added to the soil before or after sowing or else it can be applied by itself alone or together with the herbicide pre- or postemergence. The treatment of the plant or seeds with the antidote can therefore in principle be carried out independently of the time of application of the phytotoxic chemical. It can, however, also be carried out simultaneously (tank mixture). The pre-emergence treatment includes both treatment of the crop area before sowing (ppi=pre-plant incorporation) and treatment of the crop areas after sowing but before emergence of the plants.

The rates of application of the antidote with respect to the herbicide depend largely on the mode of application. Where a field treatment is carried out, either as tank mixture or with separate application of herbicide and antidote, the ratio of antidote to herbicide is in the range from 1:100 to 1:1, but is preferably 1:5.

When dressing seeds and taking similar specific protective measures, however, much lower amounts of antidote are required compared with e.g. the amounts of herbicide later employed per hectare of crop area. For seed dressing, 0.1 to 10 g of antidote per kg of seeds are required, with the preferred amount being from 1 to 2 grams. If it is desired to apply the antidote shortly before sowing by seed swelling, antidote solutions which contain the active ingredient in a concentration of 1 to 10,000 ppm, preferably of 100 to 1000 ppm, are used.

As a rule, protective measures such as seed dressing with an antidote of the formula I and possible later field treatment with agricultural chemicals are only loosely connected. Pretreated seeds and plants can later come in contact with different chemicals in agriculture, horticulture and forestry. Accordingly, the invention relates to plant protection compositions which contain an antidote of the formula I as active ingredient, together with conventional carriers. If appropriate, such compositions may be additionally mixed with the chemical against whose action it is desired to protect the cultivated plant, e.g. with a herbicide.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals such as wheat, rye, barley, oats and, in particular, rice, sorghum, maize, and also cotton, sugar beet, sugar cane, soybeans, beans, and peas.

The above list of plants implies no restriction thereto. In principle, an antidote can be employed wherever it is desired to protect a cultivated plant from the phytotoxicity of a chemical.

The invention also relates to a method of protecting cultivated plants from aggressive (phytotoxic) chemicals, which comprises applying a phenylamino-oxoacetic acid of the formula I or an ester thereof, which acts as antidote, either before or after application of the agrochemical, or also simultaneously with the agrochemical.

The invention also relates to the propagation products of such cultivated plants which are given a protective treatment with an antidote of the formula I. By propagation products are meant all generative parts of plants which can be used for the propagation of the cultivated plant, for example grains (seeds in the narrow sense), roots, fruit, tubers, rhizomes, parts of stalks, branches (seedlings) and other parts of plants. Propagation products also include pregerminated plants and young plants which, after pregermination or emergence, will be further transplanted. Such young plants can be selectively protected by means of a complete or partial immersion treatment before transplantation.

Particularly suitable antidotes are those phenylamino-oxo-acetic acids of the formula I and esters thereof, wherein (a) $R_1$ is hydrogen, $R_2$ is hydrogen or an unsubstituted $C_1$-$C_{18}$alkyl, $C_1$-$C_{18}$alkenyl or $C_3$-$C_{10}$cycloalkyl radical and $X_1$ and $X_2$ have the meanings assigned to them;

(b) $R_1$ is hydrogen, $R_2$ is a $C_1$-$C_6$alkyl, $C_3$-$C_{18}$alkenyl or $C_3$-$C_{10}$cycloalkyl radical which is substituted by $C_1$-$C_6$-alkoxy, $C_1$-$C_6$alkylthio, $C_1$-$C_6$hydroxyalkoxy, $C_1$-$C_6$hydroxyalkylthio, $C_1$-$C_6$alkoxycarbonyl, $C_1$-$C_6$alkylcarbonyl, amino, $C_1$-$C_6$alkylamino, $C_1$-$C_6$dialkylamino, a saturated 5- or 6-membered heterocyclic ring which is bound through the nitrogen atom and which may contain an additional nitrogen, oxygen or sulfur atom in the ring, a $C_3$-$C_6$alkenylcarbonyl group, carbamoyl, $C_1$-$C_6$alkylcarbamoyl, $C_1$-$C_6$dialkylcarbamoyl or a 5- or 6-membered heterocyclic ring which is linked to the carbamoyl group and which may contain an additional nitrogen, oxygen or sulfur atom in the ring, or phenyl which is unsubstituted or substituted by halogen, cyano, $C_1$-$C_6$alkyl, $C_1$-$C_6$alkoxy, $C_1$-$C_6$alkylthio, $C_1$-$C_6$alkoxycarbonyl, $C_1$-$C_6$dialkylamino, carbamoyl, $C_1$-$C_6$alkylcarbamoyl or $C_1$-$C_6$dialkylcarbamoyl or nitro, and $X_1$ and $X_2$ have the meanings assigned to them;

(c) $R_1$ is hydrogen and $R_2$ is a $C_3$-$C_6$alkynyl radical which is substituted by phenyl which is unsubstituted or substituted by halogen, cyano, $C_1$-$C_6$alkyl, $C_1$-$C_6$alkoxy, $C_1$-$C_6$alkylthio, $C_1$-$C_6$alkoxycarbonyl, $C_1$-$C_6$alkylcarbonyl, amino, $C_1$-$C_6$alkylamino, $C_1$-$C_6$dialkylamino, carbamoyl, $C_1$-$C_6$alkylcarbamoyl, $C_1$-$C_6$dialkylcarbamoyl or nitro, and $X_1$ and $X_2$ have the meanings assigned to them.

Among those compounds, individual compounds meriting particular interest are: 4-chlorophenylamino-oxo-aminoacetic acid, methyl 4-chlorophenylamino-oxo-acetate, methyl 4-chlorophenylmethylamino-oxo-acetate, ethyl 4-chlorophenylamino-oxo-acetate, isopropyl 4-chlorophenylamino-oxo-acetate, benzyl 4-chlorophenylamino-oxo-acetate, phenylethyl 4-chlorophenylamino-oxo-acetate, cyclohexyl 4-chlorophenylamino-oxo-acetate, 4-fluorophenylamino-oxo-acetic acid, methyl 4-fluorophenylamino-oxo-acetate, ethyl 4-fluorophenylamino-oxo-acetate, cyclohexyl 4-fluorophenylamino-oxo-acetate, 3-fluorophenylamino-oxo-acetate, methyl 3-fluorophenylamino-oxo-acetate, ethyl 3-fluorophenylamino-oxo-acetate, 3-chlorophenylamino-oxo-acetic acid, phenylethyl 3-chlorophenylamino-oxo-acetate, ethyl 3-bromophenylamino-oxo-acetate, ethyl 4-bromophenylamino-oxo-acetate, ethyl 3-iodophenylamino-oxo-acetate, methyl 4-iodophenylamino-oxo-acetate, ethyl 4-iodophenylamino-oxo-acetate, ethyl 3-chloro-4-fluorophenylamino-oxo-acetate, ethyl 3,4-dichlorophenylamino-oxo-acetate, 3,4-dibromophenylamino-oxo-acetic acid, ethyl 3,4-dibromophenylamino-oxo-acetate, methyl 3,4-dibromophenylamino-oxo-acetate.

The phenylamino-oxo-acetic acids and the esters thereof are prepared in a manner which is known per se, e.g. by reacting an aniline of the formula III

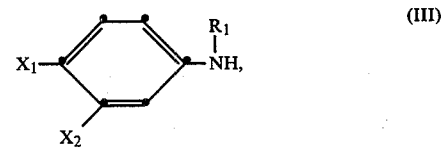

wherein $R_1$, $X_1$ and $X_2$ have the meanings assigned to them above, with oxalic acid or an oxalic acid monoester of the formula IV

 (IV)

in an inert organic solvent and in the presence of a basic condensing agent.

Such reactions are described e.g. in Farmaco ed. Sci. 22 (1967), p. 717, French Pat. No. 1 517 896 or German Offenlegungsschrift No. 2 819 878.

The aniline of the formula III can also be reacted with an oxalic acid diester of the formula

 (IVa)

wherein $R_2'$ has the meaning of $R_2$ with the exception of hydrogen, or with the halide of an oxalic acid monoester of the formula IVb

 (IVb)

wherein Hal is a halogen atom, preferably a chlorine or bromine atom, and R' has the meaning assigned to it above.

The reaction can be carried out by simply heating the reactants, but it is preferably conducted in the presence of an inert organic solvent. Examples of such solvents are toluene, xylene, benzene, chloroform or methylene chloride.

As basic condensing agents there are used amines such as diethylamine or triethylamine, pyridine, choline, and also inorganic bases, e.g. sodium carbonate or sodium bicarbonate.

A further route for preparing the phenylamino-oxo-acetic acids of the formula I and esters thereof comprises reacting an aniline of the formula II with an oxalic acid dihalide of the formula IVc Hal—CO—CO—Hal (IVc)

wherein Hal is a halogen atom, preferably a chlorine or bromine atom, and reacting the phenylamino-oxo-acetic acid halide so obtained of the formula V

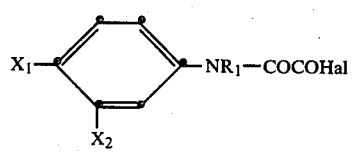 (V)

wherein R, $X_1$ and $X_2$ have the meanings assigned to them, with water or an alcohol of the formula VI

 (VI)

wherein $R_2$ has the meaning assigned to it.

This reaction too is carried out in an inert organic solvent and in the presence of a basic condensing agent.

A final product, in which $R_1$ and/or $R_2$ are hydrogen, can be converted in a manner known per se into another such product, wherein $R_1$ and/or $R_2$ have a meaning different from hydrogen, by reacting a compound of the formula I

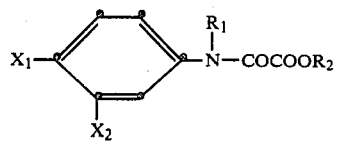 (I)

wherein at least one of the substituents $R_1$ and $R_2$ is hydrogen and the other as well as $X_1$ and $X_2$ have the meanings assigned to them, with a compound of the formulae VII and/or VIII

 (VII)

 (VIII)

wherein $R_1$ and $R_2$ have the meanings assigned to them above with the exception of hydrogen, and Z is the reactive radical of an organic or inorganic acid.

Examples of such acid radicals are the radicals of hydrochloric, hydrobromic, hydriodic, methylsulfuric, toluenesulfuric, methylsulfonic and toluenesulfonic acid.

A phenylamino-oxo-acetate of the formula I can be converted into another ester in accordance with French Pat. No. 1 517 869 in the presence of an alkanol different from the ester end and of a base.

These reactions also are carried out in organic solvents, under normal pressure and in the temperature range from 0° C. to the boiling point of the reaction mixture. If necessary, an organic or inorganic base may be added as acid acceptor or condensing agent.

Many of the phenylamino-oxo-acetic acids of the formula I and esters thereof are known, for example from French Pat. No. 1 517 896, German Offenlegungsschrift No. 3 819 878, Farmaco ed. Sci. 22, (1967), page 717 et seq., and others are novel compounds.

Novel are those compounds of the formula I, wherein $R_1$ is a $C_1$-$C_4$alkyl radical, and $R_2$, $X_1$ and $X_2$ have the meanings assigned to them.

Those compounds of the formula I are also new, wherein $R_1$, $X_1$ and $X_2$ have the meanings assigned to them, and $R_2$ has a meaning different from unsubstituted lower alkyl, alkoxyalkyl or cyclohexyl.

The compounds of formula I may be used by themselves alone or together with the compounds which it is desired to antagonise.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosed in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised cononut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl laurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$-alkyl radical and, as further substituents, lower unsubstituted or halogenated alkyl, benzyl or lower hydroxyalkyl radicals. The salts are preferably in the form of halides, methylsulfates or ethylsufates, e.g. stearyltrimethylammonium chloride or benzyldi(2-chloroethyl)-ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents," Chemical Publishing Co., Inc. New York, 1980.

The agrochemical compositions usually contain 0.1 to 99%, preferably 0.1 to 95%, of a compound of the formula I, 1 to 99.9% to 1%, preferably 99.8 to 5%, of a solid or liquid adjuvant, and 0 to 25%, preferably 0.1 to 25% of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

The following Example illustrates the preparation of the compound of the formula I. Compounds prepared in corresponding manner are listed in the table following this Example. Parts and percentages are by weight.

EXAMPLE

Preparation of methyl 4-chlorophenylamino-oxo-acetate

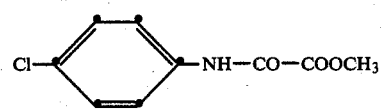

With stirring, 6.7 g of monomethyl oxalate chloride are added dropwise at 0° to 5° C. to a solution of 6.4 g of 4-chloroaniline and 7.9 g pyridine in 150 ml of dry methylene chloride. When the addition is complete, the suspension is stirred for 30 minutes at room temperature, then diluted with 100 ml of methylene chloride, washed twice with 3N hydrochloric acid and once with saturated sodium bicarbonate solution, dried and concentrated. The residual oil crystallises on trituration, affording 10.4 g of crystalline title compound with a melting point of 162°–164° C.

The following compounds are prepared in corresponding manner

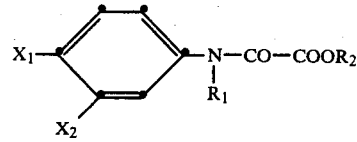

| No. | $X_1, X_2$ | $R_1$ | $R_2$ | (°C.) |
|---|---|---|---|---|
| 1 | Cl(4) | H | $CH_3$ | Example 1 m.p. 162–164° |
| 2 | Cl(4) | $CH_3$ | $CH_3$ | $n_D^{20}$ 1.5391 |
| 3 | Cl(4) | H | $C_4H_9n$ | m.p. 144–146° |
| 4 | Cl(4) | H | $C_6H_{13}n$ | m.p. 121° |
| 5 | Cl(4) | H | $C_8H_7n$ | m.p. 106–109° |
| 6 | Cl(4) | H | $C_{16}H_{33}n$ | m.p. 107–109° |
| 7 | Cl(4) | H | $CH_2-CH=CH_2$ | m.p. 114–115° |
| 8 | Br(4) | $CH_3$ | $CH_2-CH=CH_2$ | |
| 9 | Cl(4) | $CH_3$ | $CH_2-CH=CH_2$ | oil |
| 10 | | H | $CH_2-C\equiv CH$ | |
| 11 | Cl(4) | $CH_3$ | $CH_2C\equiv CH$ | m.p. 68–69,5° |
| 12 | Cl(4) | H | $nC_8H_{16}CH=CHC_8H_{17}$ | wax |
| 13 | H | H | $iC_3H_7$ | m.p. 137° |
| 14 | Cl(4) | H | $CH_2OH$ | |
| 15 | Cl(4) | H | $C_2H_4OH$ | |
| 16 | Cl(4) | H | $C_2H_4OCH_3$ | |
| 17 | Cl(4) | H | $C_2H_4OCH_3$ | |
| 18 | Cl(4) | H | $C_2H_4OC_2H_4OH$ | |
| 19 | Cl(4) | H | $C_2H_4(OC_2H_4)_2OH$ | m.p. 71–72° |
| 20 | Cl(4) | H | $C_2H_4(OC_2H_4)_3OH$ | |
| 21 | Cl(4) | H | $C_2H_4(OC_2H_4)_2OCH_3$ | |
| 22 | Cl(4) | H | $C_2H_4(OC_2H_4)_3OCH_3$ | |
| 23 | Cl(4) | H | $C_2H_4SCH_3$ | |
| 24 | Cl(4) | H | $C_2H_4NH_2$ | |
| 25 | Cl(4) | $CH_3$ | $C_2H_4N(CH_3)_2$ | |
| 26 | Cl(4) | H | $CH_2COOC_2H_5$ | m.p. 116–118° |
| 27 | Cl(4) | H | $CH(CH_3)COOCH_3$ | m.p. 108–110° |
| 28 | Cl(4) | H | $CH_2COCH_3$ | |
| 29 | Cl(4) | H | $CH_2COC_6H_5$ | |
| 30 | Cl(4) | H | $CH_2COC_6H_4Cl(4)$ | |
| 31 | Cl(4) | H | $CH_2COC_6H_4Cl(3)$ | |
| 32 | Cl(4) | H | $CH_2COC_6H_4CH_3(3)$ | |
| 33 | Cl(4) | H | $CH_2COC_6H_4OCH_3(4)$ | |
| 35 | Cl(4) | $CH_3$ | $C_2H_4Cl$ | |
| 36 | Cl(4) | $CH_3$ | $C_2H_4Cl$ | |
| 37 | Cl(4) | H | $CH=CHC_6H_5$ | |
| 38 | Cl(4) | H | $C_2H_4C_6H_5$ | |
| 39 | Cl(4) | H | $C_2H_2C\equiv CC_6H_5$ | |
| 40 | Cl(4) | H | $C_2H_4OCH_2CH=CH_2$ | |
| 41 | Cl(4) | H | $CH_2C_6H_5$ | m.p. 125° |
| 42 | Cl(4) | $CH_3$ | $CH_2C_6H_4Cl$ | |
| 43 | Cl(4) | $C_2H_5$ | $CH_2C_2H_5$ | |
| 44 | Cl(4) | H | $C_2H_4C_6H_4$ | m.p. 162° |
| 45 | Cl(4) | H | $CH_2C_4H_3Cl_2(3,4)$ | |
| 46 | Cl(4) | $CH_3$ | $CH_2OCOC_{15}H_{31}$ | |
| 47 | Cl(4) | H | $CH_2OCOC_{18}H_{37}$ | |
| 48 | Cl(4) | H | $CH_2OCOC_{17}H_{35}$ | |
| 49 | Cl(4) | $CH_3$ | $CH_2$ cyclopropyl | |
| 50 | Cl(4) | $CH_3$ | $CH_2$ cyclohexyl | |
| 51 | Cl(4) | H | cyclohexyl | m.p. 155–158° |
| 52 | Cl(4) | H | $C_2H_4CON(CH_3)_2$ | |
| 53 | Cl(4) | $C_2H_5$ | $CH_2CONH_2$ | |
| 54 | F(4) | H | $CH_3$ | m.p. 150–153° |
| 55 | F(4) | H | $C_2H_5$ | m.p. 118–119° |
| 56 | F(4) | $CH_3$ | $CH_3$ | |
| 57 | F(4) | H | $nC_8H_{17}$ | |
| 58 | F(4) | H | $nC_{12}H_{25}$ | |
| 59 | F(4) | H | $nC_{18}H_{37}$ | |
| 60 | F(4) | $CH_3$ | $CH_2-CH=CH_2$ | |
| 61 | F(4) | $CH_3$ | $CH_2-C(CH_3)=CH_2$ | |
| 62 | F(4) | $CH_3$ | $CH_2-C\equiv CH$ | |
| 63 | F(4) | H | $C_8H_{16n}CH=CHC_8H_{17n}$ | |
| 64 | F(4) | H | $CH_2OH$ | |
| 65 | F(4) | $CH_3$ | $CH_2OH$ | |
| 66 | F(4) | $CH_3$ | $C_2H_4OH$ | |
| 67 | F(4) | $CH_3$ | $C_2H_4OCH_3$ | |
| 68 | F(4) | H | $C_2H_4OC_2H_5$ | |
| 69 | F(4) | H | $C_2H_4(OC_2H_4)_2OH$ | |
| 70 | F(4) | H | $C_2H_4(OC_2H_4)_3OH$ | |
| 71 | F(4) | H | $C_2H_4(OC_2H_4)_2OCH_3$ | |
| 72 | F(4) | H | $C_2H_4SCH_3$ | |
| 73 | F(4) | H | $C_2H_4NH_2$ | |
| 73 | F(4) | $CH_3$ | $C_2H_4N(CH_3)_2$ | |
| 74 | F(4) | $CH_3$ | $CH_2COOCH_3$ | |
| 75 | F(4) | H | $CH(CH_3)COOCH_3$ | |
| 76 | F(4) | $CH_3$ | $CH_2COCH_3$ | |
| 77 | F(4) | H | $CH_2COC_6H_5$ | |
| 78 | F(4) | H | $CH_2COC_6H_4Cl(4)$ | |
| 79 | F(4) | H | $CH_2COC_6H_4Cl(3)$ | |
| 80 | F(4) | H | $CH_2COC_6H_3Cl_2(3,4)$ | |
| 81 | F(4) | $CH_3$ | $CH_2COC_6H_4CH_3(3)$ | |
| 82 | F(4) | H | $CH_2COC_6H_4OCH_3(4)$ | |
| 83 | F(4) | $C_2H_5$ | $C_2H_4Cl$ | |
| 84 | F(4) | H | $CH=CHC_6H_5$ | |
| 85 | F(4) | H | $C_2H_4C_6H_5$ | |
| 86 | F(4) | H | $CH_2C\equiv CC_6H_5$ | |
| 87 | F(4) | $CH_3$ | $CH_2C_6H_5$ | |
| 88 | F(4) | H | $CH_2C_6H_4CH_3(4)$ | |
| 89 | F(4) | H | $CH_2C_6H_4Cl(4)$ | |
| 90 | F(4) | H | $CH_2C_6H_4F(4)$ | |
| 91 | F(4) | H | $CH_2C_6H_3Cl_2(3,4)$ | |
| 92 | F(4) | H | $CH_2OCOC_{15}H_{31}$ | |
| 93 | F(4) | H | $CH_2OCOC_{18}H_{37}$ | |
| 94 | F(4) | H | $CH_2OCOC_{17}H_{35}$ | |
| 95 | F(4) | $CH_3$ | $CH_2$—cyclopropyl | |
| 96 | F(4) | H | cyclohexyl | m.p. 117° |
| 97 | F(4) | H | $C_2H_4CON(CH_3)_2$ | |
| 98 | F(4) | $CH_3$ | $CH_2CONH_2$ | |
| 99 | Cl(3)F(4) | H | $C_2H_5$ | m.p. 130–131° |
| 100 | Cl(3)F(4) | $CH_3$ | $CH_3$ | |
| 101 | Cl(3)F(4) | H | $nC_4H_9$ | |
| 102 | Cl(3)F(4) | H | $nC_8H_{17}$ | |
| 103 | Cl(3)F(4) | H | $nC_{12}H_{25}$ | |
| 104 | Cl(3)F(4) | H | $nC_{18}H_{37}$ | |
| 105 | Cl(3)F(4) | $CH_3$ | $CH_2CH=CH_2$ | |
| 106 | Cl(3)F(4) | H | $CH_2C(CH_3)=CH_2$ | |
| 107 | Cl(3)F(4) | H | $CH_2C\equiv CH$ | |
| 108 | Cl(3)F(4) | H | $nC_8H_{16}CH=CHC_8H_{17n}$ | |
| 109 | Cl(3)F(4) | $CH_3$ | $CH_2OH$ | |
| 110 | Cl(3)F(4) | $C_2H_5$ | $C_2H_4OH$ | |
| 111 | Cl(3)F(4) | H | $C_2H_4OCH_3$ | |
| 112 | Cl(3)F(4) | $CH_3$ | $C_2H_4OC_2H_5$ | |
| 113 | Cl(3)F(4) | H | $C_2H_4(OC_2H_4)_2OH$ | |
| 114 | Cl(3)F(4) | H | $C_2H_4(OC_2H_4)_3OH$ | |
| 115 | Cl(3)F(4) | H | $C_2H_4(OC_2H_4)_2OCH_3$ | |
| 116 | Cl(3)F(4) | $CH_3$ | $C_2H_4SCH_3$ | |
| 117 | Cl(3)F(4) | H | $C_2H_4NH_2$ | |
| 118 | Cl(3)F(4) | $CH_3$ | $C_2H_4N(CH_3)_2$ | |
| 119 | Cl(3)F(4) | H | $CH_2COOCH_3$ | |
| 120 | Cl(3)F(4) | H | $CH_2COCH_3$ | |
| 121 | Cl(3)F(4) | H | $CH_2COC_6H_5$ | |
| 122 | Cl(3)F(4) | H | $CH_2COC_6H_4Cl(4)$ | |
| 123 | Cl(3)F(4) | H | $CH_2COC_6H_4Cl(3)$ | |
| 124 | Cl(3)F(4) | H | $CH_2COC_6H_3Cl_2(3,4)$ | |
| 125 | Cl(3)F(4) | $CH_3$ | $CH_2COC_6H_4CH_3(3)$ | |

-continued

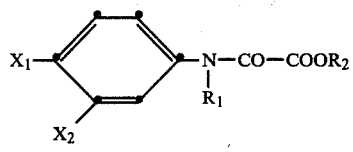

| No. | $X_1, X_2$ | $R_1$ | $R_2$ | (°C.) |
|---|---|---|---|---|
| 126 | Cl(3)F(4) | $CH_3$ | $CH_2COC_6H_4OCH_3(4)$ | |
| 127 | Cl(3)F(4) | $CH_3$ | $C_2H_4Cl$ | |
| 128 | Cl(3)F(4) | H | $CH=CHC_6H_5$ | |
| 129 | Cl(3)F(4) | H | $C_2H_4C_6H_5$ | |
| 130 | Cl(3)F(4) | H | $CH_2C{\equiv}CC_6H_5$ | |
| 131 | Cl(3)F(4) | $CH_3$ | $C_2H_4OCH_2CH=CH_2$ | |
| 132 | Cl(3)F(4) | $CH_3$ | $CH_2C_6H_5$ | |
| 133 | Cl(3)F(4) | $CH_3$ | $CH_2C_6H_4CH_3(4)$ | |
| 134 | Cl(3)F(4) | H | $CH_2C_6H_4Cl(4)$ | |
| 135 | Cl(3)F(4) | H | $CH_2C_6H_4Br(4)$ | |
| 136 | Cl(3)F(4) | H | $CH_2C_6H_3Cl_2(3,4)$ | |
| 137 | Cl(3)F(4) | H | $CH_2OCOC_{15}H_{31}$ | |
| 138 | Cl(3)F(4) | H | $CH_2OCOC_{18}H_{37}$ | |
| 139 | Cl(3)F(4) | H | $CH_2OCOC_{17}H_{35}$ | |
| 140 | Cl(3)F(4) | $CH_3$ | $CH_2$ cyclopropyl | |
| 141 | Cl(3)Br(4) | H | $CH_3$ | m.p. 162–164° |
| 142 | Cl(3)Br(4) | H | $CH_2CH=CH_2$ | m.p. 148–151° |
| 143 | Cl(3)Br(4) | $CH_3$ | $CH_2C_6H_5$ | m.p. 122–125° |
| 144 | F(3) | H | H | m.p. 186–190° |
| 145 | F(3) | H | $C_2H_5$ | m.p. 80–88° |
| 146 | F(3) | H | $CH_3$ | m.p. 107–108° |
| 147 | F(4) | H | H | m.p. 144–145° decomp. |
| 148 | Cl(3) | H | $C_2H_4C_6H_5$ | m.p. 95° |
| 149 | Cl(4) | H | H | m.p. 189–190 decomp. |
| 150 | Br(3) | H | H | |
| 151 | Br(3) | $CH_3$ | $CH_3$ | |
| 152 | Br(4) | H | H | |
| 153 | Cl(3)F(4) | H | H | |
| 154 | Cl(3)F(4) | $CH_3$ | H | |
| 155 | F(3) | H | $nC_4H_9$ | |
| 156 | Br(3) | H | $C_2H_5$ | m.p. 126–132° |
| 157 | Br(4) | H | $C_2H_5$ | m.p. 157–158 |
| 158 | F(3)Cl(4) | H | $CH_3$ | |
| 159 | F(3)Cl(4) | H | $nC_6H_{13}$ | |
| 160 | $Cl_2(3,4)$ | H | $C_2H_5$ | m.p. 176–178° |
| 161 | $Cl_2(3,4)$ | $CH_3$ | $CH_3$ | m.p. 79–80° |
| 162 | $Cl_2(3,4)$ | H | $CH_3$ | m.p. 163–165° |
| 163 | $Cl_2(3,4)$ | $CH_3$ | $CH_2{-}C{\equiv}CH$ | |
| 164 | I(4) | H | H | |
| 165 | I(4) | H | $CH_3$ | m.p. 169–170° |
| 166 | I(4) | H | $C_2H_5$ | m.p. 146–147° |
| 167 | I(4) | H | $C_2H_5$ | m.p. 150–155° |
| 168 | $Br_2(3,4)$ | H | H | |
| 169 | $Br_2(3,4)$ | H | $CH_3$ | m.p. 161–162° |
| 170 | $Br_2(3,4)$ | $CH_3$ | H | |
| 171 | $Br_2(3,4)$ | H | $CH_2{-}CH=CH_2$ | m.p. 139–141° |
| 172 | Cl(3) | H | $CH_3$ | m.p. 115–117° |
| 173 | Cl(3) | H | $C_2H_5$ | |
| 174 | Cl(3) | $CH_3$ | H | |
| 175 | Cl(3) | $C_2H_5$ | H | |
| 176 | I(3) | H | H | |
| 177 | I(4) | H | $CH_3$ | m.p. |

-continued

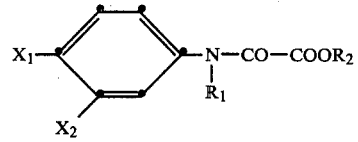

| No. | $X_1, X_2$ | $R_1$ | $R_2$ | (°C.) |
|---|---|---|---|---|
| 178 | $OCHF_2(3)Br(4)$ | H | $CH_3$ | 169–170° m.p. 100–102° |
| 179 | $OCHF_2(4)$ | H | $C_2H_5$ | m.p. 99–101° |
| 180 | $OCHF_2(4)$ | H | $CH_3$ | m.p. 133–134° |
| 181 | $OCF_3(4)$ | H | $CH_3$ | |

EXAMPLE 2

The compounds of formula I of this invention may be formulated e.g. as follows:

Dusts: The following substances are used to formulate (a) 5% and (b) a 2% dust:

(a)

5 parts of methyl 4-chlorophenylamino-oxo-acetate or a mixture thereof with a herbicide, 95 parts of talc;

(b)

2 parts of the above compound or a mixture, 1 part of highly dispersed silicic acid 97 parts of talc.

The active ingredients are mixed with the carriers and ground and in this form can be processed to dusts for application.

Granulate: The following substances are used to formulate a 5% granulate:

5 parts of 3-chlorophenylamino-oxo-acetic acid or of a mixture thereof with a herbicide, 0.25 part of epoxidised vegetable oil, 0.25 part of cetyl polyglycol ether 3.25 parts of polyethylene glycol 91 parts of kaolin (particle size 0.3–0.8 mm).

The active ingredient is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

Wettable powders: The following constituents are used to formulate (a) a 70%, (b) a 40%, (c) and (d) a 25% and (e) a 10% wettable powder:

(a)

70 parts of methyl 3,4-dichlorophenylamino-oxo-acetate or a mixture thereof with a herbicide, 5 parts of sodium dibutylnaphthylsulfonate 3 parts of naphthalenesulfonic acid/phenolsulfonic acid/formaldehyde condensate (3:2:1)

10 parts of kaolin 12 parts of Champagne chalk (b)

40 parts of active ingredient or mixture, 5 parts of sodium lignosulfonate 1 part of sodium dibutylnaphthalenesulfonate 54 parts of silicic acid (c)

25 parts of active ingredient or mixture, 4.5 parts of calcium lignosulfate 1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)
25 parts of active ingredient or mixture;
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)
10 parts of active ingredient or mixture,
3 parts of a mixture of the sodium salts of saturated fatty alcohol sulfates
5 parts of naphthalenesulfonic acid/formaldehyde condensate
82 parts of kaolin.

The active ingredients are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for foliar application (for delaying growth or for fungicidal use).

Emulsifiable concentrate: The following substances are used to formulate a 25% emulsifiable concentrate:
25 parts of 3-fluorophenylamino-oxo-acetic acid or of a mixture thereof with a herbicide,
2.5 parts of epoxidised vegetable oil
10 parts of an alkylarylsulfonate/fatty alcohol polyglycol ether mixture
5 parts of dimethyl formamide
27.5 parts of xylene.

Paste
The following substances are used to formulate a 45% paste:
(a)
45 parts of 3-chlorophenylamino-oxo-acetic acid or of a mixture thereof with a herbicide,
5 parts of sodium aluminium silicate,
14 parts of cetyl polyglycol ether with 8 moles of ethylene oxide,
3 parts of oleyl polyglycol ether with 5 moles of ethylene oxide,
2 parts of spindle oil,
10 parts of polyethylene glycol,
23 parts of water.

(b)
45 parts of the above compound or a mixture,
5 parts of ethylene glycol,
3 parts of octylphenoxy polyethylene glycol containing 9–10 moles of ethylene oxide per mole of octylphenol,
3 parts of a mixture of aromatic sulfonesulfonic acids, condensed with formaldehyde as ammonium salt,
1 part of silicone oil in form of a 75% emulsion,
0.1 part of a mixture of 1-(3-chloroallyl)-3,5,7-triazoazonium-adamantane chloride with sodium carbonate (chloride value at least 11.5%),
0.2 part of a biopolymeric thickener containing a maximum of 100 bacilli per gram,
42.7 parts of water.

The active ingredient is intimately mixed with the adjuvants in appropriate devices and ground. By diluting the resultant paste with water, it is possible to prepare suspensions of the desired concentration.

EXAMPLE 3

The ability of the compounds of formula I to antagonise the phytotoxic action of strong herbicides on cultivated plants is determined by means of the following tests:

Test on Wheat: Wheat seeds are sown in plastic pots containing 0.5 liter of garden soil in a greenhouse. 12 days later, when the plants have reached the 2- to 3-leaf stage, the compound for testing as antidote is applied together with a herbicide as tank mixture. Evaluation of the action is made 20 days after application and the results are expressed in percent. Plants treated with the herbicide alone (0% protective action) and completely untreated controls (100% protective action) are used as references. The results are reported in the following tables.

| Herbicide: 2-propynyl α-[4-(3,5-dichloropyridyl-2-oxy)-phenoxy]propionate | | |
|---|---|---|
| Antidote | Herbicide | relative protective action in % |
| Compound | Rate of application in kg/ha | Rate of application in kg/ha | |
| 1 | 0.25 | 0.5 | 25 |
| 1 | 0.5 | 0.5 | 25 |
| 1 | 1.5 | 0.75 | 50 |
| 2 | 1.5 | 0.75 | 38 |
| 3 | 1.5 | 0.75 | 25 |
| 4 | 1.5 | 0.75 | 12.5 |
| 5 | 1.5 | 0.75 | 12.5 |
| 7 | 1.5 | 0.75 | 38 |
| 9 | 1.5 | 0.75 | 12.5 |
| 11 | 1.5 | 0.75 | 25 |
| 12 | 1.5 | 0.75 | 12.5 |
| 19 | 1.5 | 0.75 | 12.5 |
| 27 | 1.5 | 0.75 | 25 |
| 41 | 1.5 | 0.75 | 38 |
| 54 | 0.25 | 0.5 | 25 |
| 54 | 0.5 | 0.5 | 25 |
| 54 | 1.5 | 0.75 | 50 |
| 99 | 0.25 | 0.5 | 25 |
| 99 | 0.5 | 0.5 | 25 |
| 99 | 1.5 | 0.75 | 50 |
| 143 | 1.5 | 0.75 | 12.5 |
| 146 | 1.5 | 0.75 | 25 |
| 160 | 1.5 | 0.75 | 50 |
| 162 | 1.5 | 0.75 | 50 |
| 169 | 1.5 | 0.75 | 50 |
| 171 | 1.5 | 0.75 | 38 |
| 172 | 1.5 | 0.75 | 50 |
| 177 | 1.5 | 0.75 | 38 |

| Antidote | Herbicide | relative protective action in % |
|---|---|---|
| Compound | Rate of application in kg/ha | Rate of application in kg/ha | |
| Herbicide: n-butyl α-[4-(4-trifluoromethylpyridyl-2-oxy)-phenoxy]propionate ("fluazifop-butyl") | | | |
| 1 | 0.125 | 0.062 | 38 |
| Herbicide: 1,2-dimethyl-3,5-diphenyl-1H—pyrazolium-methylsulfate, ("difenzoquat") | | | |
| 1 | 0.5 | 1 | 38 |
| Herbicide: 4-chlorobut-2-ynyl-3-chlorophenylcarbamate, ("barban") | | | |
| 1 | 4 | 4 | 63 |
| Herbicide: 2-chloro-4-ethylamino-6-t-butylamino-s-triazine ("therbutylazin") | | | |

-continued

| Antidote | Herbicide | relative |
|---|---|---|
| Compound | Rate of application in kg/ha | Rate of application in kg/ha | protective action in % |
| 1 | 0.5 | 0.5 | 38 |

Test in barley: The above test is carried out in exactly indentical manner, except that barley seeds are sown instead of wheat seeds.

| Antidote | Herbicide | relative |
|---|---|---|
| Compound | Rate of application in kg/ha | Rate of application in kg/ha | protective action in % |
| Herbicide: 2-propynyl α-[4-(3,5-dichloropyridyl-2-oxy)-phenoxy]propionate | | | |
| 1 | 0.5 | 0.25 | 38 |
| 19 | 0.5 | 1.5 | 50 |
| 169 | 1.5 | 1.5 | 12.5 |
| Herbicide: methyl α-[4-(3,5-dichlorophenoxy)phenoxy]propionate ("hoeton") | | | |
| 1 | 1 | 2 | 25 |
| 1 | 1 | 1 | 25 |
| Herbicide: 1,2-dimethyl-3,5-diphenyl-1H—pyrazolium-methyl-sulfate ("difenzoquat") | | | |
| 1 | 0.5 | 1 | 25 |
| Herbicide: 2-chloro-4-ethyl-6-t-butylamino-s-triazine ("terbutylazin") | | | |
| 1 | 0.5 | 0.5 | 25 |

Test in maize: The above test is carried out in exactly identical manner, except that maize seeds are used instead of wheat or barley seeds.

| Herbicide: 3,5-dichlorocyanophenoxime-2-(2"-chlorocyclopropyl)-propionate | | | |
|---|---|---|---|
| Antidote | | Herbicide | relative |
| Compound | Rate of application in kg/ha | Rate of application in kg/ha | protective action in % |
| 1 | 1 | 1 | 25 |

Test with wheat and barley: Wheat and barley seeds are sown in containers measuring 27×17×22 cm in a greenhouse. Cultivation is carried out under optimum growth conditions (regular watering, relative humidity of about 50%, day temperature of 20° C., night temperature of 12° C.). 12 days later, when the plants have emerged and have reached the 2- to 3-leaf stage, the antidote is applied together with the herbicide as tank mixture in different concentrations. Evaluation of the action is made 24 days after application and the results are expressed in percent. Plants treated with the herbicide alone (0% protective action) and completely untreated plants (100% protective action) are used as reference. The results are as follows:

| Herbicide: 2-propynyl α-[4-(3,5-dichloropyridyl-3-oxy)-phenoxy]propionate | | | | |
|---|---|---|---|---|
| Antidote | | Herbicide | relative protective action in % | |
| Compound | Rate of application in kg/ha | Rate of application in kg/ha | wheat | barley |
| 1 | 0.5 | 0.5 | 50 | 25 |
| 1 | 0.5 | 0.25 | 62.5 | 37.5 |
| 1 | 0.5 | 0.125 | 37.5 | 25 |
| 1 | 0.375 | 0.375 | 50 | 25 |
| 1 | 0.375 | 0.182 | 50 | 37.5 |

| Herbicide: 2-propynyl α-[4-(3,5-dichloropyridyl-3-oxy)-phenoxy]propionate | | | | |
|---|---|---|---|---|
| Antidote | | Herbicide | relative protective action in % | |
| Compound | Rate of application in kg/ha | Rate of application in kg/ha | wheat | barley |
| 1 | 0.375 | 0.091 | 37.5 | 25 |

Test with sorghum: Preemergence application of antidote and herbicide as tank mixture Flower pots having a diameter of 6 cm at the top are filled with sandy loam, in which sorghum seeds of the "Funk G 522" variety are sown. After covering the seeds, a tank mixture of the compound for testing as antidote together with the herbicide is sprayed in dilute solution onto the surface of the soil. Evaluation of the protective action of the antidote is made 14 days after application and the results are expressed in percent. Plants treated with the herbicide alone (no protective action) and completely untreated controls (100% growth) are used as references. The results are as follows:

| Herbicide: 2-chloro-6'-ethyl-N—(2"-methoxy-1"-methylethyl)-acet-O—toluidide ("metolachlor") | | | |
|---|---|---|---|
| Antidote | | Herbicide | relative |
| Compound | Rate of application in kg/ha | Rate of application in kg/ha | protective action in % |
| 7 | 1.5 | 1.5 | 38 |
| 9 | 1.5 | 1.5 | 38 |
| 27 | 1.5 | 1.5 | 38 |
| 160 | 1.5 | 1.5 | 38 |

Test with rice sown in water:

Application of the antidote during seed swelling Rice seeds are immersed for 48 hours in solutions of the compound for testing as antidote. The seeds are then allowed to dry for 2 hours until they are no longer tacky. Plastic containers measuring 25×17×12 cm are filled with sandy loam to 2 cm below the edge. The pretreated seeds are sown on the surface of the soil in the container and then very lightly covered. The soil is kept in a moist (non-marshy) state. The herbicide is then sprayed in dilute solution onto the surface of the soil. The water level is increased by degrees in accordance with the growth. The protective action of the antidote is evaluated 21 days later. Plants treated with the herbicide alone (no protective action) and completely untreated controls (100% growth) are used as references. The results are set forth below.

| Herbicide: 2-chloro-2',6'-diethyl-N—(2"-propoxyethyl)-acetanilide ("pretilachlor") | | | |
|---|---|---|---|
| Antidote | | Herbicide | relative |
| Compound | Rate of application in kg/ha | Rate of application in kg/ha | protective action in % |
| 3 | 100 | 0.25 | 25 |
| 178 | 100 | 0.25 | 50 |

Test with rice sown dry:

Application of the antidote as seed dressing Rice seeds are mixed with the compound for testing as antidote in a glass beaker. Seeds and antidote are throughly mixed by shaking and rotation. Containers measuring 47×29×24 cm are then filled with sandy loam and the dressed seeds are sown therein. The seeds are covered and the herbicide is then sprayed in dilute solution onto the surface of the soil. About 20 days after sowing (when the rice plants are in the 3-leaf stage), the surface of the soil is covered with a layer of water to a height of 4 cm. The protective action of the antidote is evaluated 30 days after application of the herbicide and the results are expressed in percent. Plants treated with the herbicide alone (no protective action) and completely untreated controls (100% growth) are used as references. The results are as follows:

| Herbicide: 2-propynyl α-[4-(3,5-dichloropyridyl-2-oxy)-phenoxy]propionate | | |
|---|---|---|
| Antidote | Herbicide | relative |
| Compound | Rate of application in kg/ha | Rate of application in kg/ha | protective action in % |
| 1 | 0.4 | 0.25 | 38 |

Test with rice sown dry (20 days after sowing, when the rice plants have reached the 3-leaf stage, the soil is flooded). Application of antidote and herbicide as tank mixture.

Rice seeds of the IR-36 variety are sown in containers measuring 47×29×24 cm, covered, and the soil is lightly pressed firm. The compound for testing as antidote together with the herbicide are then sprayed as tank mixture. About 20 days after sowing (when the rice plants are in the 3-leaf stage), the surface of the soil is covered with water to a height of 4 cm. The protective action of the antidote is evaluated 30 days after transplantation. Plants treated with herbicide alone (no protective action) and completely untreated controls (100% protective action) are used as references. The results are set forth below.

| Herbicide: 2-chloro-6″-ethyl-N—(2″-methoxy-1″-methylethyl)-acet-O—toluidide ("metolachlor") | | |
|---|---|---|
| Antidote | Herbicide | relative |
| Compound | Rate of application in kg/ha | Rate of application in kg/ha | protective action in % |
| 178 | 1.5 | 0.25 | 25 |

Test with dry rice:

Application of the antidote as seed dressing Rice seeds of the IR-36 variety together with the compound for testing as antidote are mixed in a glass beaker. Seeds and antidote and throughly mixed by shaking and rotation. Plastic containers measuring 47×29×24 cm are then filled with sandy loam and the dressed seeds are sown therein. The seeds are covered and the herbicide is they sprayed onto the surface of the soil. The protective action of the andidote is evaluated 18 days after sowing and the results are expressed in percent. Plants treated with the herbicide alone (no protective action) and completely untreated controls (100% growth) are used as references. The results are as follows:

| Herbicide: 2-propynyl α-[4-(3,5-dichloropyridyl-2-oxy)-phenyl]propionate | | |
|---|---|---|
| Antidote | Herbicide | relative |
| Compound | Rate of application in kg/ha | Rate of application in kg/ha | protective action in % |
| 1 | 0.6 | 0.25 | 50 |

What is claimed is:

1. In the method of controlling weed growth in the area of cultivated plants by application of a herbicide of the triazine, triazinone, phenylurea, carbamate, thiocarbamate, haloacetanilide, chloroacetamide, halophenoxyacetate, diphenylether, pyridyloxyphenoxyacetate, pyridyloxyphenoxyacetamide, benzoic acid, nitroaniline, oxadiazolone, phosphate, pyrazole, and sulfonylurea classes, the improvement reducing phytotoxic damage to said cultivated plants which comprises treating the plants, or the seeds, tubers or seedlings from which the plants are grown, with an antidotal amount of a compound of the formula:

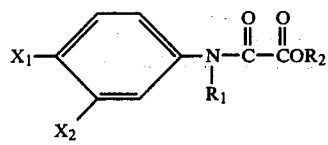

wherein each of $X_1$ and $X_2$, independently of the other, is hydrogen, halo or halomethyl, at least one of $X_1$ and $X_2$ being other than hydrogen;
$R_1$ is hydrogen or alkyl of 1 to 4 carbon atoms; and
$R_2$ is
 (a) hydrogen
 (b) alkyl of 1 to 18 carbon atoms,
unsubstituted or substituted with
  (i) $-(CH_2CH_2O)_nR'$ or $-(CH_2CH_2CH_2O)_nR'$ in which n has a value of 2, or 3 and $R'$ is hydrogen or alkyl of 1 to 6 carbon atoms;
  (ii) alkylthio of 1 to 6 carbon atoms;
  (iii) hydroxyalkylthio of 1 to 6 carbon atoms;
  (iv) alkoxycarbonyl of 1 to 6 carbon atoms in the alkoxy group;
  (v) alkylthiocarbonyl of 1 to 6 carbon atoms in the alkyl group;
  (vi) alkylcarbonyl of 1 to 6 carbon atoms in the alkyl group;
  (vii) amino, alkylamino or dialkylamino of 1 to 6 carbon atoms in each alkyl group;
  (viii) alkenylcarbonyloxy of 2 to 18 carbon atoms in the alkenyl group;
  (ix) carbamoyl, alkylcarbamoyl or dialkylcarbamoyl of 1 to 4 carbon atoms in each alkyl group;
  (x) hydroxy;
  (xi) cycloalkyl of 3 to 6 carbon atoms; or
  (xii) phenyl which is unsubstituted or substituted with halo, cyano, alkyl of 1 to 6 carbon atoms, alkoxy of 1 to 6 carbon atoms, alkylthio of 1 to 6 carbon atoms, alkylcarbonyl of 1 to 6 carbon atoms in the alkyl group, or nitro;
 (c) alkenyl or alkynyl of 3 to 6 carbon atoms, unsubstituted or substituted with phenyl, said phenyl in turn being unsubstituted or substituted with halo, cyano, alkyl of 1 to 6 carbon atoms, alkoxy of 1 to 6 carbon atoms, alkylthio of 1 to 6 carbon atoms, alkylcarbonyl of 1 to 6 carbon atoms in the alkyl group, or nitro; or
 (d) cycloalkyl of 3 to 8 carbon atoms.

2. The method claim 1 wherein $R_2$ is hydrogen, alkyl of 1 to 6 carbon atoms, benzyl, phenethyl, cyclohexyl or allyl.

3. A herbicidal composition comprising (i) a herbicidally effective amount of a herbicide selected from the group consisting of triazine, triazinone, phenylurea, carbamate, thiocarbamate, haloacetanilide, chloroacetamide, halophenoxyacetate, diphenylether, pyridyloxyphenoxyacetate, pyridyloxyphenoxyacetamide, benzoic acid, nitroaniline, oxadiazolone, phosphate, pyrazole, and sulfonylurea herbicides and (ii) an antidotal amount of a compound of the formula:

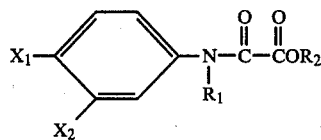

wherein each of $X_1$ and $X_2$, independently of the other, is hydrogen, halo or halomethyl, at least one of $X_1$ and $X_2$ being other than hydrogen;

$R_1$ is hydrogen or alkyl of 1 to 4 carbon atoms; and
$R_2$ is
  (a) hydrogen
  (b) alkyl of 1 to 18 carbon atoms,
unsubstituted or substituted with
  (i) —$(CH_2CH_2O)_nR'$ or —$(CH_2CH_2CH_2O)_nR'$ in which n has a value of 2, or 3 and $R'$ is hydrogen or alkyl of 1 to 6 carbon atoms;
  (ii) alkylthio of 1 to 6 carbon atoms;
  (iii) hydroxyalkylthio of 1 to 6 carbon atoms;
  (iv) alkoxycarbonyl of 1 to 6 carbon atoms in the alkoxy group;
  (v) alkylthiocarbonyl of 1 to 6 carbon atoms in the alkyl group;
  (vi) alkylcarbonyl of 1 to 6 carbon atoms in the alkyl group;
  (vii) amino, alkylamino or dialkylamino of 1 to 6 carbon atoms in each alkyl group;
  (viii) alkenylcarbonyloxy of 2 to 18 carbon atoms in the alkenyl group;
  (ix) carbamoyl, alkylcarbamoyl or dialkylcarbamoyl of 1 to 4 carbon atoms in each alkyl group;
  (x) hydroxy;
  (xi) cycloalkyl of 3 to 6 carbon atoms; or
  (xii) phenyl which is unsubstituted or substituted with halo, cyano, alkyl of 1 to 6 carbon atoms, alkoxy of 1 to 6 carbon atoms, alkylthio of 1 to 6 carbon atoms, alkylcarbonyl of 1 to 6 carbon atoms in the alkyl group, or nitro;
  (c) alkenyl or alkynyl of 3 to 6 carbon atoms, unsubstituted or substituted with phenyl, said phenyl in turn being unsubstituted or substituted with halo, cyano, alkyl of 1 to 6 carbon atoms, alkoxy of 1 to 6 carbon atoms, alkylthio of 1 to 6 carbon atoms, alkylcarbonyl of 1 to 6 carbon atoms in the alkyl group, or nitro; or
  (d) cycloalkyl of 3 to 8 carbon atoms.

4. A herbicidal composition according to claim 3 wherein in said compound $R_2$ is hydrogen, alkyl of 1 to 6 carbon atoms, benzyl, phenethyl, cyclohexyl or allyl.

5. A herbicidal composition according to claim 4 wherein said herbicide is of the formula:

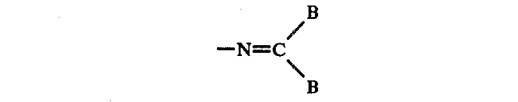

in which
$Y_1$ is hydrogen or halo;
$Y_2$ is hydrogen, halo or trifluormethyl;
Q is =N— or =CH—;
A is alkyl of 1 to 4 carbon atoms; alkenyl of 3 to 4 carbon atoms, alkynyl of 3 to 4 carbon atoms, alkoxyalkyl of 2 to 8 carbon atoms, or $$-N=C\begin{matrix}B\\B\end{matrix}$$

in which each B is alkyl of 1 to 4 carbon atoms or taken together are alkylene of 4 or 5 carbon atoms.

6. A herbicidal composition according to claim 5 wherein said herbicide is 2-propynyl alpha-4-(3,5-dichloropyrid-2yloxy)phenoxypropionate and said compound is 3,4-dibromophenylaminooxoacetate.

* * * * *